US011134977B2

(12) United States Patent
Sawada et al.

(10) Patent No.: US 11,134,977 B2
(45) Date of Patent: Oct. 5, 2021

(54) ULTRASOUND PROBE AND ULTRASOUND TREATMENT TOOL

(71) Applicant: OLYMPUS CORPORATION, Hachioji (JP)

(72) Inventors: Kiichiro Sawada, Hachioji (JP); Ken Fujisaki, Sagamihara (JP); Yasuo Tanigami, Hachioji (JP); Hideto Yoshimine, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 266 days.

(21) Appl. No.: 16/389,211

(22) Filed: Apr. 19, 2019

(65) Prior Publication Data
US 2019/0239917 A1 Aug. 8, 2019

Related U.S. Application Data

(63) Continuation of application No. PCT/JP2016/082177, filed on Oct. 28, 2016.

(51) Int. Cl.
A61B 17/32 (2006.01)
A61B 17/16 (2006.01)

(52) U.S. Cl.
CPC ...... *A61B 17/320068* (2013.01); *A61B 17/16* (2013.01); *A61B 2017/32007* (2017.08); *A61B 2017/320072* (2013.01); *A61B 2017/320073* (2017.08); *A61B 2017/320074* (2017.08); *A61B 2217/005* (2013.01)

(58) Field of Classification Search
CPC .................. A61B 17/320068; A61B 17/16
See application file for complete search history.

(56) References Cited

U.S. PATENT DOCUMENTS 4,832,683 A * 5/1989 Idemoto ......... A61B 17/320068
604/22
2007/0233131 A1 10/2007 Song et al.
2008/0208231 A1 8/2008 Ota et al.
(Continued)

FOREIGN PATENT DOCUMENTS

JP H05-29700 Y2 7/1993
JP 2008-119250 A 5/2008
JP H05-029696 Y2 7/2019

OTHER PUBLICATIONS

Jan. 31, 2017 International Search Report issued in International Patent Application No. PCT/JP2016/082177.

*Primary Examiner* — Andrew Yang
(74) *Attorney, Agent, or Firm* — Oliff PLC

(57) ABSTRACT

An ultrasound probe includes a probe body, and a treatment unit. The treatment unit includes: a cutter that is provided at a distal end part of the treatment unit and that cuts the bone according to move of the treatment unit along a longitudinal axis in a state where ultrasonic vibration is being transmitted to the probe body; and a path that is provided in the treatment unit and through which debris of a bone that is cut by the cutter are discharged along the longitudinal axis toward a proximal end side with respect to the cutter. The path includes a first opening that is provided in a distal end surface of the cutter; and a second opening that is provided in a side surface part of the treatment unit, wherein the path allows the first opening and the second opening to communicate.

10 Claims, 9 Drawing Sheets

(56) References Cited

U.S. PATENT DOCUMENTS

2008/0300591 A1\* 12/2008 Darian ........... A61B 17/320068
 606/41
2009/0312692 A1 12/2009 Cotter et al.
2010/0167235 A1 7/2010 Vercellotti et al.
2012/0089053 A1 4/2012 Cotter et al.
2013/0345734 A1 12/2013 Cotter et al.

\* cited by examiner

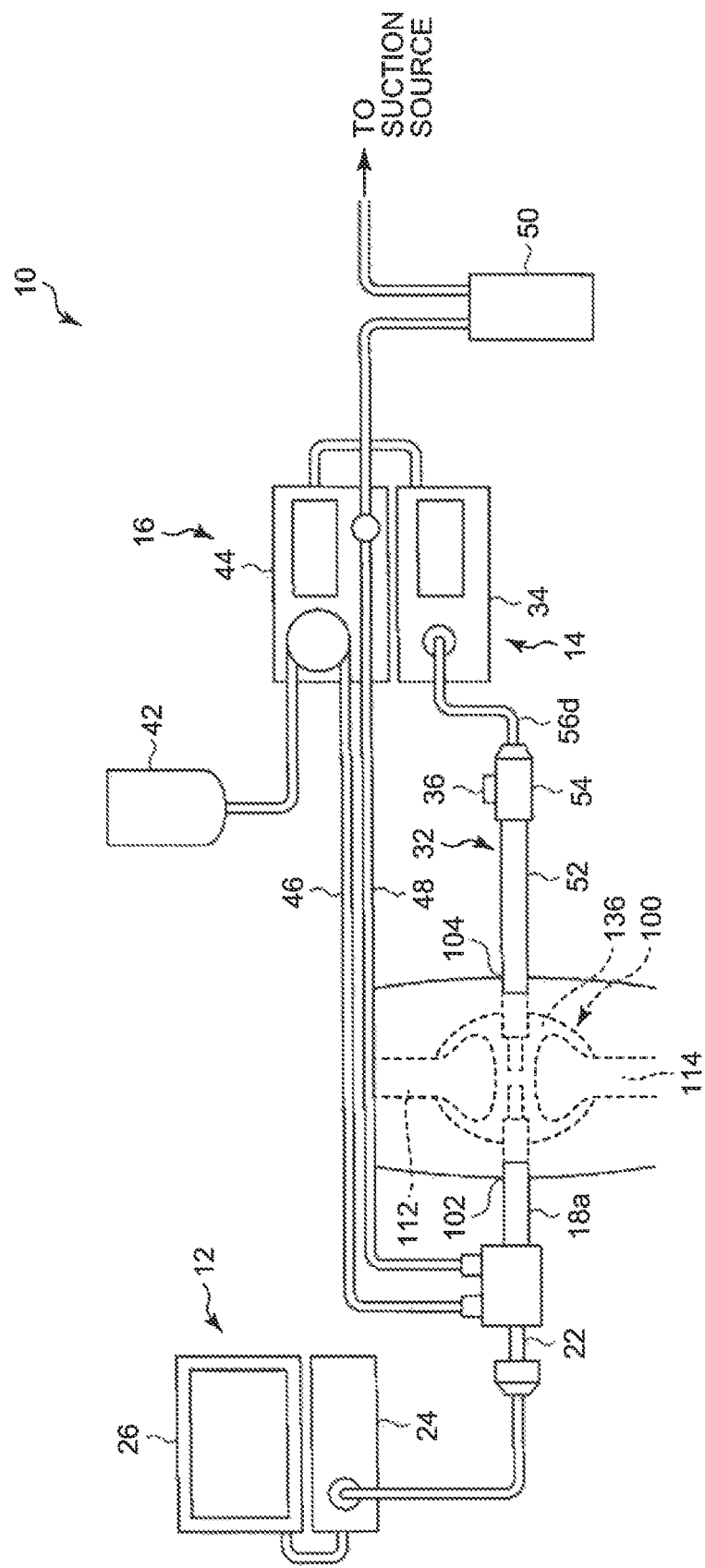

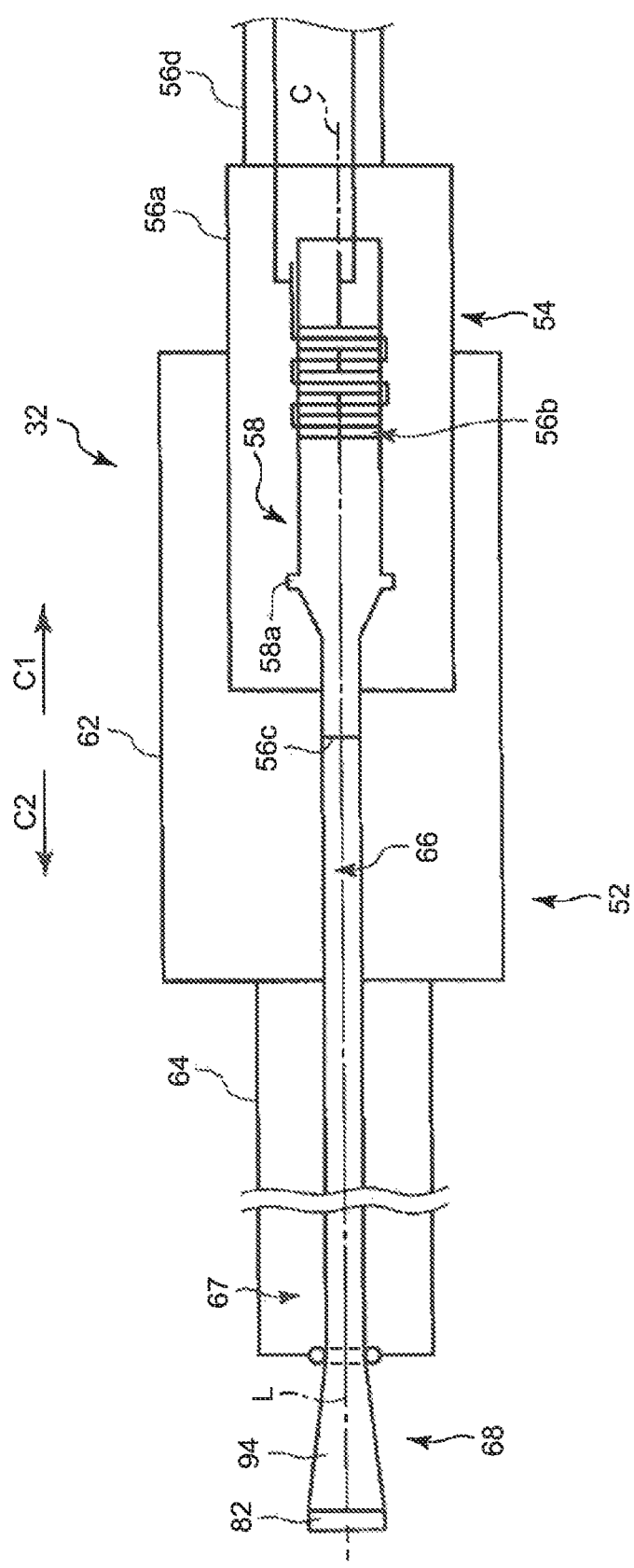

US 11,134,977 B2

ULTRASOUND PROBE AND ULTRASOUND TREATMENT TOOL

CROSS-REFERENCE TO RELATED APPLICATION

This application is a continuation of International Application No. PCT/JP2016/082177, filed on Oct. 28, 2016, the entire contents of which are incorporated herein by reference.

BACKGROUND

The present disclosure relates to an ultrasound probe and an ultrasound treatment tool.

An ultrasonic probe can have a treatment unit provided on its distal end. The ultrasonic probe can transmit ultrasonic vibration to the treatment unit so that when the treatment unit contacts a bone, the treatment unit can form a concave hole in the bone.

When the treatment unit cuts the bone, debris can be produced by cutting the bone and the debris can accumulate between the distal end of the treatment unit and the bone. This may reduce the cutting rate of the treatment unit. To increase the cutting rate, a way of efficiently discharging the bone debris is needed.

SUMMARY

An ultrasound probe according to an exemplary embodiment in the present disclosure includes: a probe body and a treatment unit having a cutter provided at a distal end part of the treatment unit that cuts bone. The treatment member also has a path through which debris resulting from cutting from the bone are discharged. The path includes a first opening on a distal end surface of the cutter and a second opening on a side surface part of the treatment unit.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 1 is a schematic diagram of a treatment system according to an exemplary embodiment;

FIG. 2 is a diagram schematically illustrating a configuration of a treatment unit according to an exemplary embodiment;

DETAILED DESCRIPTION

Figure 3A:
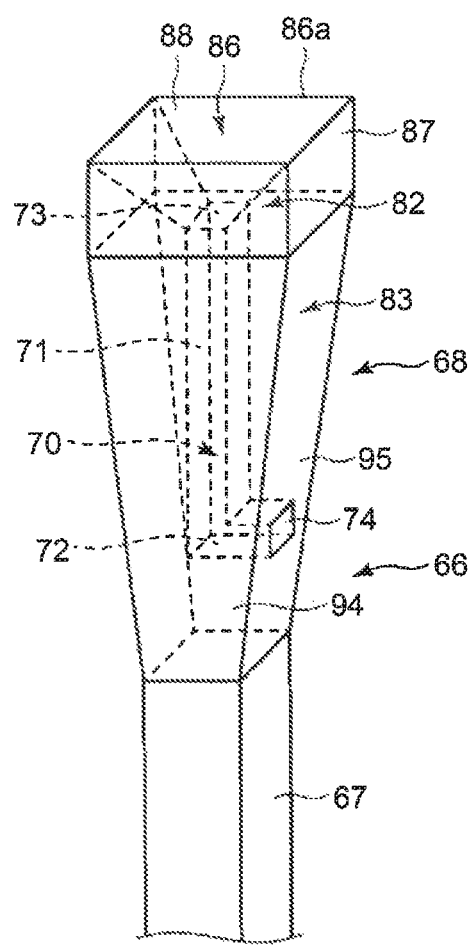
FIG. 3A is a perspective view schematically illustrating a configuration of a treatment unit according to an exemplary embodiment.

FIG. 1 is a diagram of a treatment system 10 that is used to treat a knee joint 100. The treatment system 10 includes an arthroscopic device 12, a treatment device 14, and a perfusion device 16.

The arthroscopic device 12 includes an arthroscope 22 that observes an articular cavity 136 in the knee joint 100 of a patient, an arthroscope controller 24 that performs image processing based on a subject image of which image is captured by the arthroscope 22, and a monitor 26 that shows a video that is generated by the image processing performed by the arthroscope controller 24. The arthroscope 22 is inserted into the articular cavity 136 of the knee joint 100 via a first portal 102 that allows the inside of the knee joint 100 and the outside of the skin to communicate. The arthroscope 22 and a treatment tool 52 to be described below in the treatment device 14 are drawn as being opposed to each other in FIG. 1; however, the arthroscope 22 and the treatment tool 52 are arranged in an appropriate positional relationship according to the position of the subject to be treated, etc.

The treatment device 14 includes a treatment unit 32, a controller 34, and a switch 36. The switch 36 is illustrated as a hand switch in FIG. 1. Alternatively, the switch 36 may be a foot switch. The controller 34 supplies electric energy for generating ultrasonic vibration in the treatment unit 32 in response to an operation on the switch 36. The treatment unit 32 is inserted into the articular cavity 136 of the knee joint 100 of the patient from a second portal 104 that allows the inside of the knee joint 100 and the outside of the skin to communicate.

The perfusion device 16 includes a liquid source 42 that stores a perfusion liquid, such as a saline solution, a perfusion pump unit 44, and a suction bottle 50. One end of a liquid transmission tube 46 is connected to the liquid source 42. The other end of the liquid transmission tube 46 that is a liquid transmission pipeline is connected to the arthroscope 22. The perfusion pump unit 44 thus is able to send out the perfusion liquid into the suction bottle 50 from the articular cavity 136 of the knee joint 100 via the arthroscope 22.

One end of a liquid discharge tube 48 is connected to the suction bottle 50. The other end of the liquid discharge tube 48 that is a liquid discharge pipeline is connected to the arthroscope 22. The perfusion pump unit 44 thus is able to discharge the perfusion liquid from the inside of the articular cavity 136 of the knee joint 100 into the suction bottle 50 via the arthroscope 22.

The perfusion liquid may be sent out and discharged from a portal (not illustrated in the drawings) that is different from the first portal 102 and the second portal 104. In an example, a liquid transmission cannula (not illustrated in the drawings) is inserted into the articular cavity 136 of the knee joint 100 via a third portal (not illustrated in the drawings). In this case, the liquid transmission tube 46 is connected to the liquid transmission cannula and the perfusion device 16. The perfusion liquid is sent out into the articular cavity 136 of the knee joint 100 via the liquid transmission cannula.

In another example, a liquid discharge cannula (not illustrated in the drawings) is inserted into the articular cavity 136 of the knee joint 100 via a fourth portal (not illustrated in the drawings). In this case, the liquid discharge tube 48 is connected to the liquid discharge cannula and the perfusion device 16. The perfusion liquid is discharged from the inside of the articular cavity 136 of the knee joint 100 to the suction bottle 50 via the liquid discharge cannula.

FIG. 2 is a diagram of a configuration of the treatment unit 32. As illustrated in FIG. 2, a center axis C is defined. A direction along the center axis C serves as a longitudinal direction. One side in the longitudinal direction serves as a distal end side (the side indicated by the arrow C1 in FIG. 2) and the side opposite to the distal end side serves as a proximal end side (the side indicated by the arrow C2 in FIG. 2).

The treatment unit 32 includes the ultrasound treatment tool 52 and a ultrasonic transducer unit 54. It is preferable that the ultrasound transducer unit 54 be detachable from the ultrasound treatment tool 52; however, the ultrasound transducer unit 54 may be integrated with the ultrasound treatment tool 52.

The ultrasound transducer unit 54 includes a housing (transducer case) 56a. A bolt-clamped Langevin-type transducer 56b including a piezoelectric element that transforms the supplied electric energy into ultrasonic vibration is provided in the housing 56a. An end of a cable 56d is connected to the transducer (ultrasound transducer) 56b. The other end of the cable 56d is connected to the controller 34. Supply of an electric current (alternating electric current) to the transducer 56b from the controller 34 via the cable 56d causes the transducer 56b to generate ultrasonic vibration. The ultrasonic vibration causes the transducer 56b to resonate at a given frequency. An ultrasound probe 66 to be described below is attached to the distal end of the transducer 56b.

The ultrasound treatment tool 52 includes a housing (handle) 62, a cylinder (outer cylinder) 64 that extends from the housing 62 along the center axis C and the ultrasound probe 66 that is inserted into the cylinder 64. The cylinder 64 is attached to the housing 62 from the distal end side. The housing 62 and the cylinder 64 are formed of a material with electric insulation. The housing 56a of the ultrasound transducer unit 54 is detachably connected to the housing 62 of the ultrasound treatment tool 52.

The ultrasound probe 66 is provided to extend from the distal end side to the proximal end side. The ultrasound probe 66 is formed of a material having high vibration transmissivity, such as titanium alloy. The proximal end of the ultrasound probe 66 is connected to a connecting part 56c of the ultrasound transducer unit 54. The ultrasonic vibration that is generated by the transducer 56b is transmitted to the distal end of the ultrasound probe 66. The ultrasonic vibration causes the ultrasound probe 66 to vibrate longitudinally in a direction parallel with the center axis C. In other words, the ultrasound probe 66 is a vibration transmission member that enables transmission of the ultrasonic vibration from the proximal end side to the distal end side.

A rotation knob (not illustrated in the drawings) that is a rotation operation member may be attached to the housing 62 of the ultrasound treatment tool 52. The rotation knob is rotatable with respect to the housing 62 about a center axis of the cylinder 64. Rotating the rotation knob causes the housing 56a of the ultrasound transducer unit 54, the cylinder 64, and the ultrasound probe 66 to rotate together with respect to the housing 62 about the center axis C.

The ultrasound probe 66 includes a probe body 67 and a treatment unit 68 that is provided on the distal end side with respect to the probe body 67. The outer peripheral surface of the probe body 67 is covered with the cylinder 64 and the housing 62. The probe body 67 extends along the center axis C. The treatment unit 68 protrudes from the distal end of the cylinder 64 to the distal end side. In other words, the treatment unit 68 is formed of the part protruding from the cylinder 64 in the ultrasound probe 66. The treatment unit 68 contacts a bone to be treated in the state where ultrasonic vibration is transmitted to the ultrasound probe 66 and accordingly forms a hole in the bone.

It is preferable that the probe body 67 be formed straightly. A longitudinal axis L of the treatment unit 68 is defined. The treatment unit 68 may extend from the distal end of the probe body 67 straightly to the distal end side or may be bent appropriately. For this reason, the center axis C of the probe body 67 and the longitudinal axis L of the treatment unit 68 may match or differ from each other. The longitudinal axis L herein matches the center axis C.

Figure 3B:
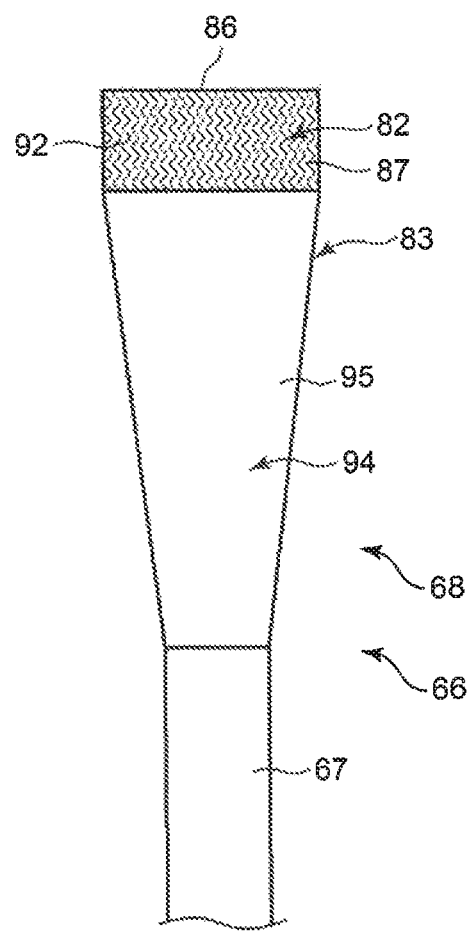
FIG. 3B is a side view schematically illustrating a configuration of a treatment unit according to an exemplary embodiment.
Figure 4:
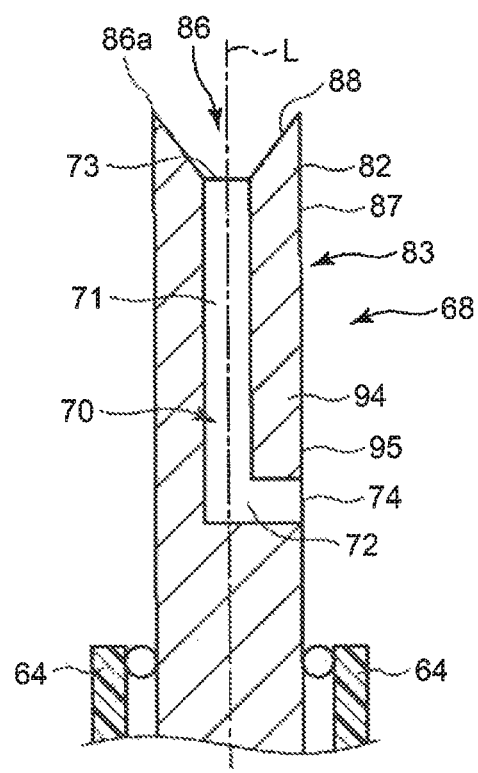
FIG. 4 is a diagram schematically illustrating a cross-section containing a longitudinal axis of the treatment unit according to an exemplary embodiment.
Figure 5A:
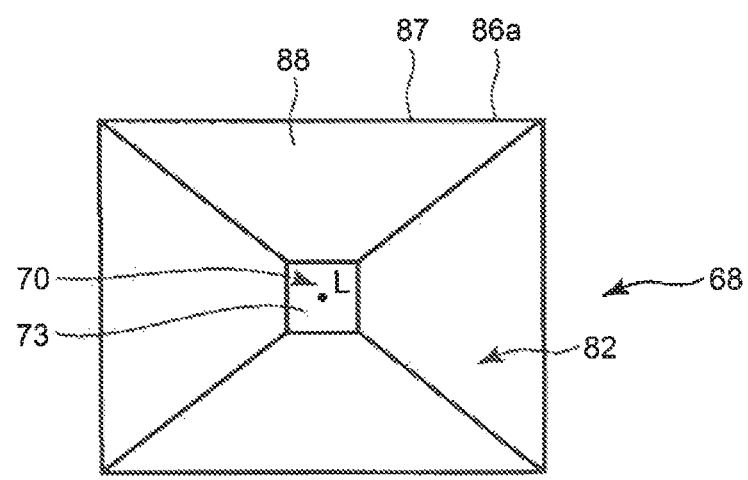
FIG. 5A is a schematic diagram of the treatment unit according to an exemplary embodiment, viewed from a distal end side.
Figure 5B:
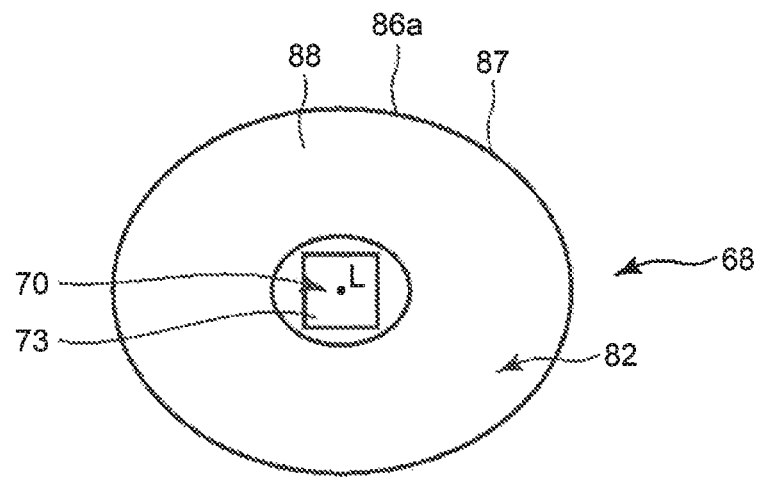
FIG. 5B is a schematic diagram of a treatment unit according to an exemplary embodiment, viewed from the distal end.

Using FIG. 3A to FIG. 5B, a configuration of the treatment unit 68 will be described. FIG. 3A is a perspective view of a configuration of the treatment unit 68. FIG. 3B is a side view of a configuration of the treatment unit 68 of an example. FIG. 4 illustrates a cross-section containing the longitudinal axis L of the treatment unit 68. FIGS. 5A and 5B are diagrams of projection geometries of the treatment unit 68 on the proximal end side viewed from the distal end side along the longitudinal axis L. As illustrated in FIGS. 3A to 5B, the treatment unit 68 includes a side surface part 83 that forms the outer peripheral surface of the treatment unit 68. The treatment unit 68 includes a cutter 82 (a first part) and a shaft 94 (second part). The cutter 82 forms a distal end part of the treatment unit 68. The shaft 94 is provided on the proximal end side with respect to the cutter 82.

The cutter 82 defines a maximum contour of the treatment unit 68. The cutter 82 is formed into a cylindrical shape, such as a polygonal cylinder or an elliptic cylinder. For example, the cutter 82 is formed into a polygonal cylinder having an appropriate shape, such as a triangular prism, a quadrangular prism, a pentagonal prism, or a hexagonal prism, or a shape close to any one of the shapes. The cutter 82 includes a distal end surface 86 that is provided at the distal end of the cutter 82 and is oriented to the distal end side; and a side surface 87 that forms the outer peripheral surface of the cutter 82. The side surface 87 forms part of the side surface part 83 of the treatment unit 68. The cutter 82 is formed such that its cross sections orthogonal to the longitudinal axis L have the same shape or an approximately the same shape from the distal end to the proximal end. Accordingly, a projection geometry of the side surface 87 on the proximal end side viewed from the distal end side along the longitudinal axis L defines a projection geometry of the cutter 82. The projection geometry of the side surface 87 defines the cross-sectional shape of the hole that is formed in the bone. It is preferable that projection geometry of the cutter 82 on the proximal end side viewed from the distal end side along the longitudinal axis L be, for example, a polygonal shape, such as an approximately rectangular shape as illustrated in FIG. 5A, or an oval shape as illustrated in FIG. 5B. When the projection geometry of the cutter 82 is an approximately rectangular shape, it is preferable that the cutter 82 be formed into a size of approximately 4 mm×5 mm. The cutter 82 need not necessarily be formed to have clear corners. The projection geometry of the cutter 82 may have a shape of a rectangle with round corners that is an approximately polygonal shape, a shape of a track in an athletics field that is an approximately oval shape, or the like. For this reason, the projection geometry of the cutter 82 is formed into an appropriate shape, such as a polygonal shape, an approximately polygonal shape, an oval shape, or an approximately oval shape.

The treatment unit 68 moves along the longitudinal axis L to the distal end side with respect to the bone to be treated by the treatment unit 68 in the state where ultrasonic vibration is transmitted to the treatment unit 68 and accordingly a hole with a contour in approximately the same shape as that of the projection geometry illustrated in FIG. 5A or FIG. 5B is formed in the bone. For this reason, a cross-sectional shape of the cutter 82 of the treatment unit 68 that is orthogonal to the longitudinal axis L is formed according to the cross-sectional shape of a hole to be formed into the bone. There is a possibility that ultrasonic vibration may cause unnecessary cutting between the side surface 87 and the bone. For this reason, it is preferable that the side surface 87 be formed such that the total area of contact with the bone is small. Forming the side surface 87 having a small area reduces the area of contact with the bone and accordingly prevents unnecessary cutting from occurring in a part contacting the bone. There are various structures to reduce the area of contact between the bone and the side surface 87. For example, the length of the side surface 87 in a direction along the longitudinal axis L may be reduced as much as possible. As illustrated as the example according to FIG. 3B, a concave part 92 may be formed by sand blasting or by forming a groove. In this case, bone debris produced by cutting the bone through the concave part 92 in the side surface 87 is easily discharged to the proximal end side with respect to the cutter 82. In order to reduce the area of the side surface 87, the side surface 87 is formed into a structure that does not deform the projection geometry of the cutter 82.

The shaft 94 is provided to extend to the proximal end side with respect to the cutter 82. The shaft 94 is provided between the distal end of the probe body 67 and the proximal end of the cutter 82. The shaft 94 is formed as a reduction part whose area of cross section orthogonal to the longitudinal axis L reduces from the distal end side to the proximal end side. Particularly, the shaft 94 is formed as a reduction part whose cross section orthogonal to the longitudinal axis L reduces from the distal end side to the proximal end side. Thus, the projection geometry of the shaft 94 on the the proximal end side viewed from the distal end side along the longitudinal axis L is within the projection geometry of the cutter 82. Thus, the projection geometry of the cutter 82 defines a maximum contour of the treatment unit 68. The shaft 94 includes a side surface 95 that forms an outer surface of the shaft 94. The side surface 95 forms part of the side surface part 83 of the treatment unit 68.

The shaft 94 may be provided with a part whose areas of cross sections orthogonal to the longitudinal axis L are approximately uniform or increase from the distal end to the proximal end side along the longitudinal axis L. Also in this case, the shaft 94 is formed such that the projection geometry of the shaft 94 on the proximal end side viewed from the distal end side along the longitudinal axis L is within the projection geometry of the cutter 82 from the proximal end to the distal end.

The distal end surface 86 includes a brim 86a that forms the outer edge of the distal end surface 86 and a concave portion 88 that gets close to the proximal end side from the brim 86a to the center of the distal end surface 86. For this reason, the center of the distal end surface 86 is concave toward the proximal end side. The concave portion 88 may be formed by planes that are oblique to the longitudinal axis L or may be formed by a curve surface. The distal end surface 86 of the cutter 82 can be concave from the distal end to the proximal end side, forming a shape of an inverse pyramid.

The brim 86a is formed between the concave portion 88 and the side surface 87. For this reason, the brim 86a forms a shape of a blade protruding toward the distal end side. Thus, the brim 86a serves as a cutting blade that cuts a bone in treatment to make a hole in the bone.

The treatment unit 68 includes a discharge path 70. The discharge path 70 is a hollow tube path that is formed in the treatment unit 68 and that is provided to extend from the distal end side to the proximal end side. The shape of a cross-section of the discharge path 70 orthogonal to the longitudinal axis L can be approximately rectangular; however, the shape of the cross-section can be other shapes as well. For example, the shape of the cross-section of the discharge path 70 orthogonal to the longitudinal axis L may be approximately circular, approximately oval, or approximately polygonal. The discharge path 70 is a path to discharge the debris produced by the cutter 82 by cutting the bone to the proximal end side with respect to the cutter 82.

The discharge path 70 includes a first path 71 and a second path 72. The first path 71 is provided to extend along the center axis of the treatment unit 68 from the distal end of the discharge path 70 toward the proximal end side. The longitudinal axis L can serve as the center axis of the treatment unit 68. For this reason, the first path 71 is provided to extend along the longitudinal axis L. The second path 72 is provided to extend from the proximal end of the first path 71 toward the side surface part 83 of the treatment unit 68. A junction 77 is formed at the proximal end of the first path 71. In the junction 77, the proximal end of the first path and one end of the second path 72 are joined.

The first path 71 is open to the outside of the treatment unit 68 from the distal end surface 86 of the treatment unit 68. Thus, an opening 73 that is a first opening is formed in the distal end surface 86. The opening 73 is open toward the distal end side. The opening 73 is surrounded by the cutter 82 (the brim 86a and the concave portion 88) in the distal end surface 86 of the treatment unit 68. The opening 73 is positioned at the center of the concave portion 88 of the distal end surface 86. For this reason, the opening 73 is positioned at the most proximal end side in the distal end surface 86.

The second path 72 is provided to extend from the proximal end of the first path 71 toward the side surface 95 of the shaft 94. The second path 72 is provided to extend from the longitudinal axis L outward radially about the longitudinal axis L. The second path 72 is open from the side surface 95 of the shaft 94 to the outside of the treatment unit 68. Accordingly, an outlet 74 is formed on the side surface 95 of the shaft 94. The outlet 74 is open in a direction intersecting with (approximately orthogonal to) the longitudinal axis L. The outlet 74 is provided on the distal end side with respect to the distal end of the cylinder 64. Thus, the outlet 74 is positioned in a part protruding from the cylinder 64 to the distal end side in the ultrasound probe 66. The outlet 74 is a second opening that is provided in the side surface of the treatment unit 68 and is open to the outside of the treatment unit 68. The discharge path 70 allows the first opening (the opening 73) and the second opening (the outlet 74) to communicate.

It is preferable that the second path 72 be provided to extend toward the proximal end side from the longitudinal axis L to the side surface part 83. The second path 72 may be provided to extend along the direction orthogonal to the longitudinal axis L.

The shaft 94 protrudes to the distal end side along the longitudinal axis L with respect to the distal end of the cylinder 64 that covers the outer periphery of the probe body 67. For this reason, the outlet 74 of the treatment unit 68 is arranged in a position on the distal end side with respect to the distal end of the cylinder 64.

A concave hole in a desired shape that is formed in the bone, for example, has an opening brim having the same shape and size as those of the projection geometry of the cutter 82 of the treatment unit 68 on the proximal end side viewed from the distal end side along the longitudinal axis L, and the concave hole is concave straightly to the back, forming the same shape as that of the opening brim. For this reason, an exemplary desired concave hole has a shape of a rectangle with an appropriate depth.

In order to form a concave hole having the desired shape, the cutter 82 of the treatment unit 68 has to have a maximum contour part that enables projection of the cutter 82 on the proximal end side, viewed from the distal end side along the longitudinal axis L, in the desired shape of the opening brim of the concave hole. The cutter 82 of the treatment unit 68 is formed into the same shape as the desired shape of the opening brim of the desired concave hole. For this reason, the cutter 82 of the treatment unit 68 can form a concave hole having the desired opening brim.

From the point of view of reducing friction between the bone and the cutter 82 of the treatment unit 68 and of discharging debris produced from the bone, it is preferable that the length of the maximum contour part of the cutter 82 in the direction along the longitudinal axis L (ultrasonic vibration direction) be short. For this reason, it is also considered that the cutter 82 is desirably configured such that its shape is not uniform and its area of cross section is not uniform but gradually reduces from the distal end to the proximal end side.

It is preferable that the ultrasound probe 66 be caused to move straightly along the longitudinal axis L and the cutter 82 form a concave hole straightly along the longitudinal axis L. For this reason, in order to prevent the cutter 82 from swaying and form a concave hole straightly, the contour of the cutter 82 from the distal end to the proximal end has to have a given length parallel with the longitudinal axis L.

The treatment unit 68 cuts the bone while ultrasonic vibration with an appropriate amplitude is being transmitted to the ultrasound probe 66. For this reason, the cutter 82 of the treatment unit 68 has to have appropriate strength. Gradual reduction of the area of cross section from the distal end of the cutter 82 to the proximal end side may, depending on the ratio of reduction of the area of cross section, make it difficult to form the treatment unit 68 with strength required to cut a bone while ultrasonic vibration of the appropriate amplitude is being transmitted to the ultrasound probe 66.

In the cutter 82, the part configuring the maximum contour can be maintained from the proximal end to the distal end and has a length to some extent along the longitudinal axis L. The cross section of the cutter 82 orthogonal to the longitudinal axis L can be uniform or approximately uniform from the distal end of the cutter 82 to the proximal end. As described above, the treatment unit 68 has the cutter 82 and thus it is possible to maintain strength of the treatment unit 68 during straight move of the ultrasound probe 66 toward the distal end side along the longitudinal axis L and form a straight concave hole having the same shape as that of the maximum contour of the cutter 82 during bone cutting.

The area of cross section of the shaft 94 reduces from the distal end side to the proximal end side. In the ultrasound probe 66, the proximal end of the shaft 94 and the distal end of the probe body 67 cooperatively form a narrow part. Accordingly, in the shaft 94, it is possible to form a space to discharge the debris between the inner wall of the concave hole in the bone and the shaft 94.

Operations and effects of the treatment system 10 will be described with reference to FIGS. 6A to 8. The treatment system 10 is used for, for example, treatment in which a bone hole (a through hole or a concave hole) to which a ligament to be transplanted is fixed is formed in the femur or the tibia in an operation of reconstructing the anterior cruciate ligament of the knee joint. In the treatment, the arthroscope 22 is inserted into the articular cavity 136 of the knee joint 100 from the first portal 102. While an area where the treatment is performed with the arthroscope 22 is being observed, the treatment unit 68 is inserted from the second portal 104 into the articular cavity 136 of the knee joint 100. Then, the switch 36 is pressed. Accordingly, electric energy is supplied to the transducer 56b and ultrasonic vibration occurs. The ultrasound probe 66 vibrates vertically in a direction parallel with the canter axis C and accordingly the ultrasonic vibration is transmitted to the treatment unit 68 that is provided at the distal end of the ultrasound probe 66. In this state, the ultrasound probe 66 is caused to move along the longitudinal axis L to a bone B and accordingly a part of the bone B that contacts the cutter 82 of the treatment unit 68 is cut so that a bone hole for inserting the ligament to be transplanted is formed.

Figure 6A:
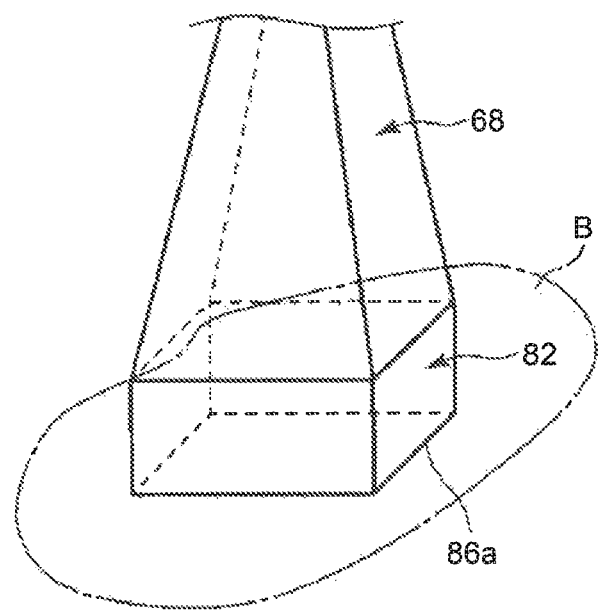
FIG. 6A is a schematic diagram illustrating that treatment using an ultrasound probe according to an exemplary embodiment is started.

FIG. 6A is a diagram illustrating that the brim 86a that is provided at the distal end of the cutter 82 is moved close to the bone B when the treatment in which a hole is made in the bone B is started. As illustrated in FIG. 6A, when the treatment in which a hole is formed in the bone B is started, the distal end of the cutter 82 of the treatment unit 68 is moved close to a position in which a hole is to be formed in the bone B. The treatment unit 68 and the bone B are observed with the arthroscope 22. During the observation, it is necessary to know the positon of the cutter 82 of the treatment unit 68 with respect to the position in which a hole is to be formed in the bone B.

Figure 6B:
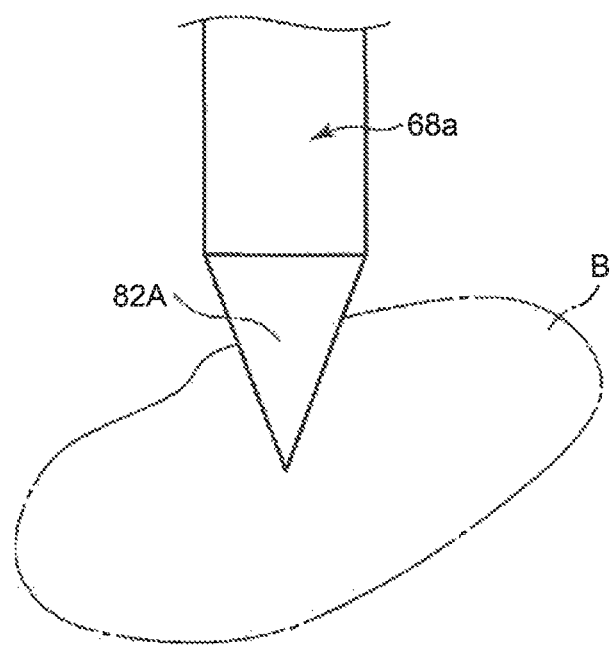
FIG. 6B is a schematic diagram illustrating that treatment using an ultrasound probe according to an exemplary embodiment is started.

FIG. 6B is a schematic diagram illustrating that treatment in which a hole is formed in the bone B with a cutter 82A having a distal end shape protruding toward the distal end side is started.

The position of the hole to be formed in the bone B is determined by an area contacting the cutter 82A, that is, the position of the cutter 82A with respect to the bone B. In the comparative example, when the treatment is started, it is necessary to predict in advance an area where a bone hole is to be formed in the bone B (position and size) in the bone B, based on the position of the distal end of the cutter 82A.

For this reason, when treatment is started, it is difficult to determine whether a hole to be formed is formed within a desired area.

As illustrated in FIG. 6A, the position of the hole to be formed in the bone B is determined by the position of the brim 86*a* of the cutter with respect to the bone B. The brim 86*a* is provided at the distal end of the treatment unit 68. Thus, when treatment is started, it is possible to check a positional relationship of the brim 86*a* with respect to the bone B easily. Accordingly, it is possible to easily know the position in which a hole is to be formed in the bone B. Knowing the positon in which a bone hole is formed in the bone B makes it possible to determine whether a hole to be formed is formed within the desired area when the treatment is started. Thus, it is possible to form the hole to be formed in an appropriate position.

Figure 7:
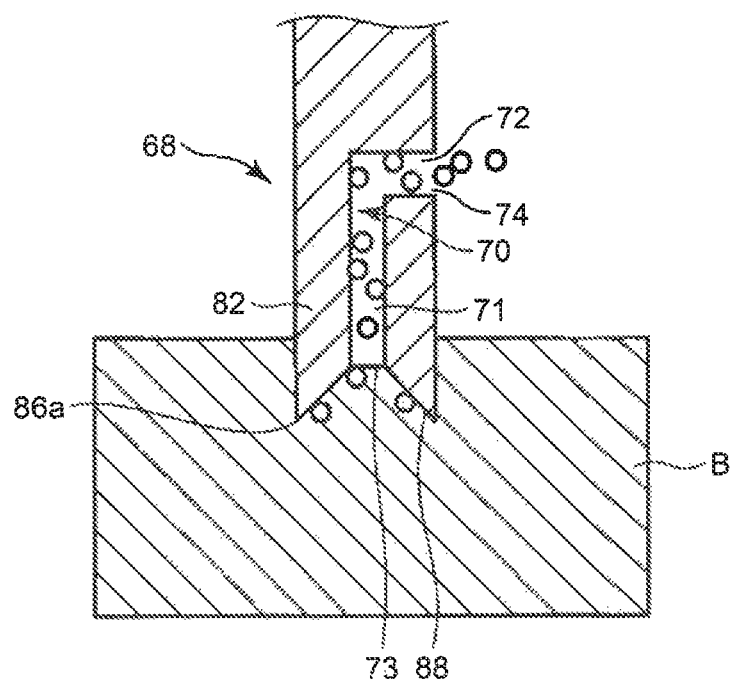
FIG. 7 is a cross-sectional view schematically illustrating that debris are discharged in the treatment using the ultrasound probe according to an exemplary embodiment.
Figure 8:
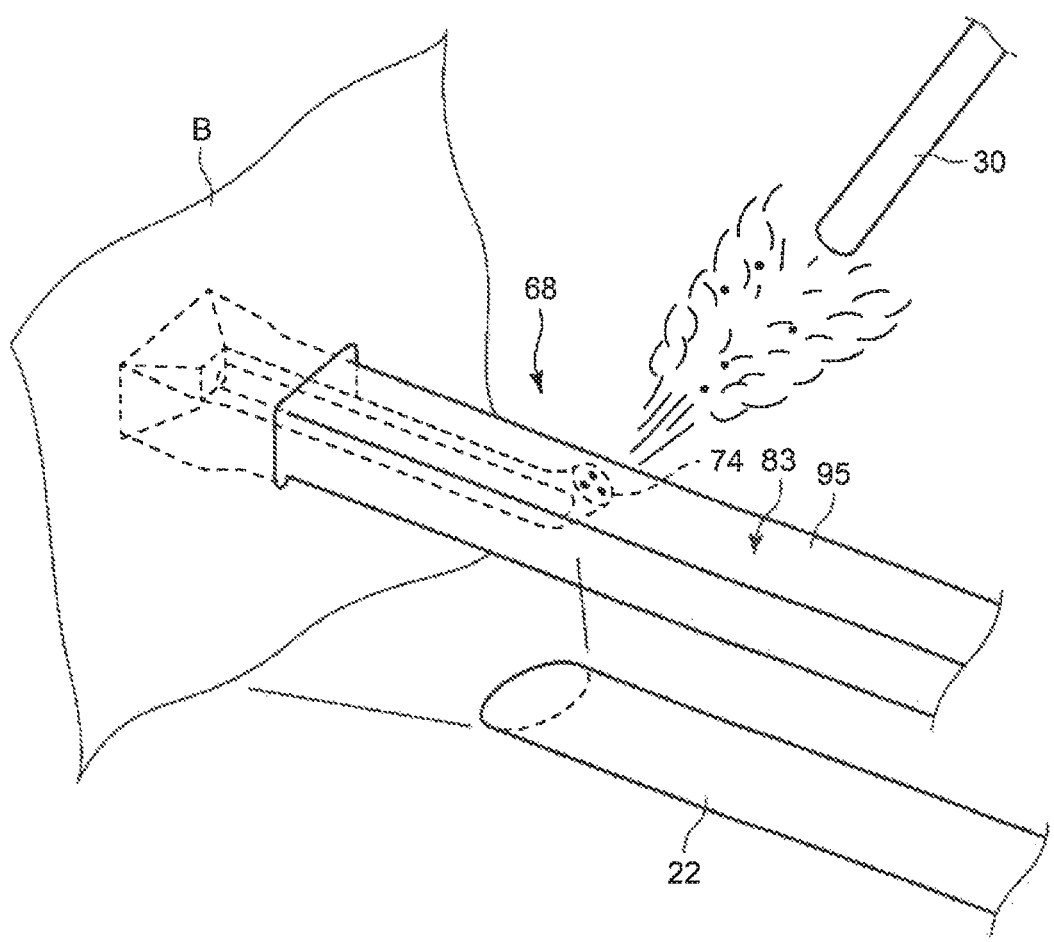
FIG. 8 is a perspective view schematically illustrating that debris are discharged in the treatment using the ultrasound probe according to an exemplary embodiment.

FIG. 7 and FIG. 8 are diagrams illustrating that a bone hole is formed in the bone B with the treatment unit 68 of the ultrasound probe 66. FIG. 7 illustrates a cross-section passing through the longitudinal axis L of the treatment unit 68. FIG. 8 is a perspective view illustrating that debris that is discharged from the bone hole is sucked with a liquid discharge cannula 30. As illustrated in FIGS. 7 and 8, when a hole is formed in the bone B, the bone B is cut in a part contacting the cutter 82 and debris of the bone B are produced. When the debris of the bone B accumulate around the distal end surface 86 of the cutter 82, contact between the cutter 82 and the bone B is prevented and accordingly the rate at which the cutter 82 cuts the bone B reduces.

The distal end surface 86 of the cutter 82 can be concave toward the center part (longitudinal direction L) on the proximal end side. For this reason, as the treatment unit 68 is moved to the distal end side with respect to the bone B, the debris that is produced in the brim 86*a* and the concave portion 88 are moved along the concave portion 88 toward the proximal end side and the center of the distal end surface 86.

The opening 73 can be formed at the center of the distal end surface 86. The opening 73 communicates with the discharge path 70. Thus, the debris of the bone B that moves toward the center of the distal end surface 86 are moved into the first path 71 of the discharge path 70 via the opening 73. The opening 73 can be provided at the center that is concave to the proximal end side in the distal end surface 86 of the cutter 82 and thus debris of the bone B are efficiently collected in the first path 71 of the discharge path 70.

The debris of the bone B are conveyed along the longitudinal axis L through the first path 71. The first path 71 is a conveyance part that conveys the debris of the bone B that is produced by the cutter 82 to the proximal end side with respect to the cutter.

The debris of the bone B conveyed to the proximal end of the first path 71 is moved to the second path 72 via the junction 77. The debris of the bone B are then moved to the side of the side surface part 83 of the treatment unit 68 via the second path 72. The debris of the bone B are then discharged to the outside of the treatment unit 68 from the side surface 87 via the outlet 74. The outlet 74 is a discharge part through which the debris of the bone B that is produced by the cutter 82 is discharged. The outlet 74 is positioned on the proximal end side with respect to the cutter 82. Thus, the debris of the bone B produced by the cutter 82 are discharged to the proximal end side with respect to the cutter 82 via the discharge path 70. In other words, the discharge path 70 is a path through which the debris of the bone B produced by the cutter 82 are discharged to the proximal end side with respect to the cutter 82.

As described above, the debris that is formed because the bone B is cut by the distal end surface 86 are conveyed to the proximal end side via the discharge path 70 and is discharged to the outside of the treatment unit 68. The debris of the bone B are conveyed through the treatment unit 68. For this reason, it is possible to discharge the debris of the bone B to the proximal end side with respect to the cutter 82 without preventing move of the cutter 82 with respect to the bone B. The debris of the bone B that is accumulated in the distal end surface 86 is discharged to the proximal end side with respect to the cutter 82 and accordingly, compared to the case where the discharge path 70 is not provided, the rate of cutting by the cutter 82 when the treatment unit 68 moves to the distal end side with respect to the bone B improves.

The discharge path 70 can be formed by the first path 71 and the second path 72; however, the discharge path 70 is not limited thereto. The discharge path 70 need not be provided to extend along the longitudinal axis L and may curve appropriately with respect to the longitudinal axis L. The discharge path 70 may allow the opening 73 and the outlet 74 in the treatment unit 68 to communicate linearly. Also in those cases, the discharge path 70 is a path that allows the opening 73 and the outlet 74 to communicate and enables discharge of the debris of the bone B accumulated on the distal end surface 86 to the proximal end side with respect to the cutter 82.

As illustrated in FIG. 8, it is preferable that treatment be performed in a state where the outlet 74 is positioned on a surface on the side opposed to the side where the arthroscope 22 is arranged with respect to the longitudinal axis L on the side surface 95 of the side surface part 83. In this case, the debris of the bone B that are discharged from the outlet 74 are discharged to the side opposite to the side where the arthroscope 22 is positioned. This prevents the debris of the bone B that are discharged from the outlet 74 from blocking the field of view of the arthroscope 22.

Furthermore, as illustrated in FIG. 8, it is also preferable that the liquid discharge cannula 30 that is inserted into the articular cavity 136 of the knee joint 100 be arranged near the outlet 74. In this case, the debris of the bone B that are discharged through the outlet 74 are discharged together with the perfusion liquid by the liquid discharge cannula 30 near the outlet 74. This inhibits the debris discharged from the outlet 74 from preventing the field of view of the arthroscope 22, thereby effectively securing the field of view of the arthroscope 22.

The first path 71 is formed such that the treatment unit 68 maintains appropriate strength and the first path 71 allows the debris of the bone to pass through. Thus, depending on the size of cross-section orthogonal to the longitudinal axis L of the first path 71, a bone that is formed cylindrically along the longitudinal axis L (trabeculae) can be formed in the first path 71. The area of cross section of the first path 71 orthogonal to the longitudinal axis L is approximated to a minimum area that allows bone debris to pass through while maintaining appropriate strength of the treatment unit 68. In this case, even when ultrasonic vibration that cuts the bone is not transmitted to a space along the longitudinal axis L of the first path 71, bone trabeculae may be crushed due to indirect effect of ultrasonic vibration because the strength of the bone trabeculae lowers.

Figure 9:
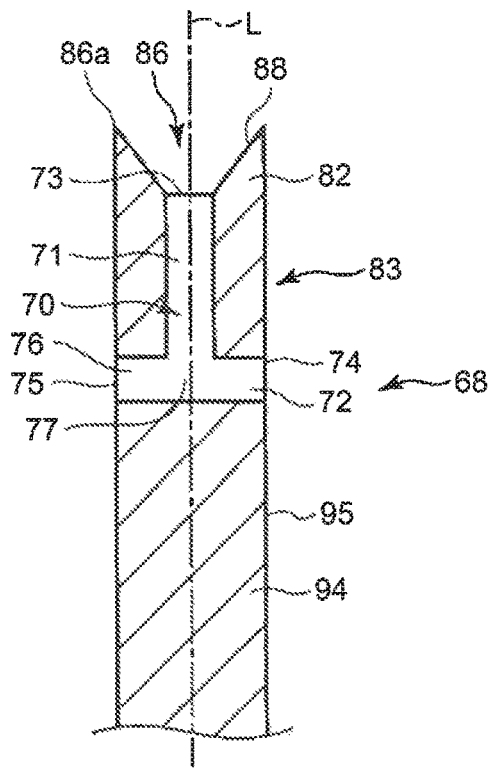
FIG. 9 is a diagram schematically illustrating a cross-section of a treatment unit according to an exemplary embodiment containing a longitudinal axis of the treatment unit.

FIG. 9 is a diagram of a configuration of the treatment unit 68 of the ultrasound probe 66 according to an exemplary embodiment. FIG. 9 illustrates a cross section passing through the longitudinal axis L.

As illustrated in FIG. 9, the discharge path 70 includes the opening 73 that is provided in the distal end surface 86 of the cutter 82 of the ultrasound probe 66 and the outlet 74 that is provided in the side surface 95 of the shaft 94. In the side surface 95, a second outlet 75 that is open to the outside of the treatment unit 68 is provided in a positon different from that of the outlet 74. Thus, two openings that are the outlet 74 and the second outlet 75 are formed in the side surface 95. In the side surface 95, the second outlet 75 is provided on the side opposite to the outlet 74 with respect to the longitudinal axis L. Accordingly, the second outlet 75 is open to the side opposite to the outlet 74. The outlet 74 and the second outlet 75 are provided in the side surface part 83 of the treatment unit 68 and serve as a second opening that is open to the outside of the treatment unit 68. For this reason, the second opening is not limited to a single opening and may include a plurality of openings.

The discharge path 70 further includes a third path 76 that is provided to extend from the proximal end of the first path 71 to the second outlet 75. The third path 76 is joined to the proximal end of the first path 71 and one end of the second path 72 at the junction 77. The second path 72 and the third path 76 are provided to extend along a direction orthogonal to the longitudinal axis L. The angles of obliqueness of the second path 72 and the third path 76 to the longitudinal axis L (directions of extension) approximately match. In other words, the second path 72 and the third path 76 are formed on the same axis. The discharge path 70 allows the opening 73, the outlet 74, and the second outlet 75 to communicate.

A plurality of openings (the outlet 74 and the second outlet 75) are formed in the side surface part 83 of the treatment unit 68. Thus, the debris of the bone B that are moved into the discharge path 70 are efficiently discharged to the outside of the ultrasound probe 66 from the outlet 74 and the second outlet 75 of the treatment unit 68. The debris of the bone B are efficiently discharged through the discharge path 70 and this enables an increase in the rate of cutting by the cutter 82.

The second path 72 and the third path 76 form a surface in the position of the proximal end of the first path 71 in the inner wall of the discharge path 70. Thus, a bone (bone trabeculae) that is formed cylindrically along the longitudinal axis L in the first path 71 contacts the surface that is formed by the second path 72 and the third path 76 at the proximal end of the first path 71 and thus is crushed. The crushed bone is then discharged together with other debris from the openings 74 and 75 to the outside of the treatment unit 68. Accordingly, even when bone trabeculae are formed in the first path 71, it is possible to efficiently crush the formed bone trabeculae and efficiently discharge the debris of the bone B to the outside of the treatment unit 68.

Figure 10:
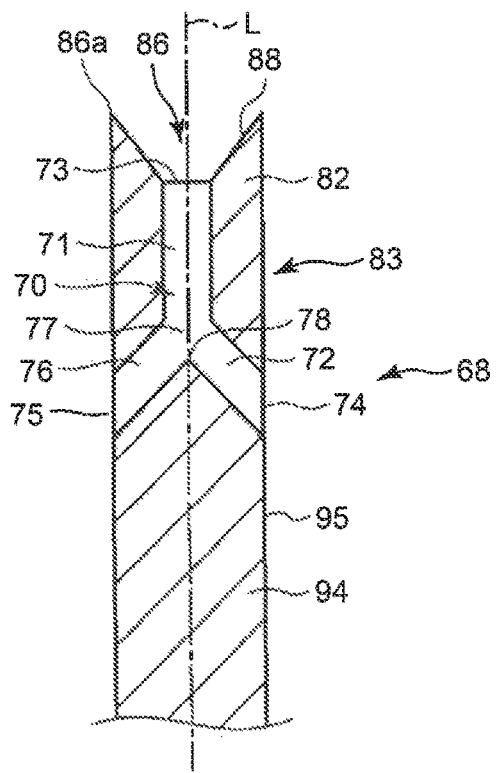
FIG. 10 is a diagram schematically illustrating a cross-section of a treatment unit according to an exemplary embodiment.

FIG. 10 is a diagram of a configuration of the treatment unit 68 of an exemplary embodiment. FIG. 10 illustrates a cross section containing the longitudinal axis L. As illustrated in FIG. 10, in the modification, each of the second path 72 and the third path 76 is provided to extend toward the proximal end side to the side surface part 83 of the treatment unit 68. Each of the second path 72 and the third path 76 is oblique to a plane approximately orthogonal to the longitudinal axis L and the longitudinal axis L. The second path 72 and the third path 76 that are oblique to the longitudinal axis L in addition to the first path 71 along the longitudinal axis L cooperatively form the discharge path 70 of the modification into an approximately Y shape.

In the modification, the inner wall of the second path 72 and the third path 76 form a protrusion 78 that protrudes toward the distal end side in the inner wall of the junction 77. The protrusion 78 is formed at the center of the treatment unit 68 in the cross section orthogonal to the longitudinal axis L. Thus, the protrusion 78 is positioned at the proximal end of the first path 71. Thus, the protrusion 78 on the proximal end side can be observed from the opening 73 when viewed from the distal end side along the longitudinal axis L.

To form a hole in the bone B, the treatment unit 68 is moved to the distal end side with respect to the bone B along the longitudinal axis L. The brim 86a and the concave portion 88 of the distal end surface 86 contact the bone B. For this reason, the bone B is cut in a part contacting the brim 86a and the concave portion 88. On the other hand, in the opening 73 of the distal end surface 86, the bone B does not contact the cutter 82 and the inner wall of the discharge path 70. Accordingly, in the opening 73 and the first path 71, ultrasonic vibration is not sufficiently transmitted to the bone B. For this reason, moving the treatment unit 68 along the longitudinal axis L toward the distal end side may cause cylindrical formation of a part of the bone B that is not cut along the longitudinal axis L in the first path 71.

In the modification, in the inner wall of the discharge path 70, the protrusion 78 that protrudes toward the distal end side is formed in the position of the proximal end of the first path 71. Thus, a bone that is formed cylindrically along the longitudinal axis L (bone trabeculae) contacts the protrusion 78 at the proximal end of the first path 71 and accordingly is crushed. The crushed bone is then discharged together with other debris to the outside of the treatment unit 68 from the openings 74 and 75. Also when bone trabeculae are formed in the first path 71, it is possible to efficiently crush the formed trabeculae and efficiently discharge the debris of the bone B to the outside of the treatment unit 68. The protrusion 78 can protrude to the distal end side along the longitudinal axis L more than that inner wall of the junction 77 between the second path 72 and the third path 76. Thus, the protrusion enables the bone trabeculae to be crushed in the possible shortest state by ultrasonic vibration.

In the above-described embodiments, etc., the first path 71 of the discharge path 70 is formed along the longitudinal axis L; however, the first path 71 is not limited to this. For example, in the first path 71, a curve part that curves with respect to the longitudinal axis L may be provided. In this case, also when bone trabeculae are formed in the first path 71, the formed bone trabeculae contact the inner wall of the curve part and are accordingly crushed and it is thus possible to discharge the debris of the bone B efficiently.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound probe comprising:
 a probe body that is configured to receive ultrasonic vibration generated by an ultrasound transducer, the probe body including a distal end side and a proximal end side; and
 a treatment unit that extends along a longitudinal axis on the distal end side of the probe body, the treatment unit including a distal end part and a side surface part adjacent to the distal end part; the treatment unit comprising:
  a cutter that is provided at the distal end part of the treatment unit and is configured to cut bone based on a movement of the treatment unit along the longitudinal axis, the cutter including a distal end surface;

a path that extends along an interior of the treatment unit, the path being configured to receive debris of the bone along the longitudinal axis towards the proximal end side of the probe body, the path including: a first opening that is provided on the distal end surface of the cutter; and a second opening that is provided on the side surface part of the treatment unit, a first part that defines a first projection geometry of the treatment unit at the proximal end side; and a second part that is provided proximally of the first part and defining a second projection geometry, an outline of the first projection geometry encompassing an outline the second projection geometry, the second opening being provided in the second part, wherein:
the path is configured to allow communication between the first opening and the second opening.

2. The ultrasound probe according to claim 1, the cutter further comprising a plurality of concave portions, wherein the first opening being provided at a center of the distal end surface of the cutter such that the plurality of concave portions surround the first opening.

3. The ultrasound probe according to claim 1, the second part including a distal end, a proximal end, and a cross-sectional area that decreases along the longitudinal axis from the distal end to the proximal end.

4. The ultrasound probe according to claim 1, wherein: the path includes: a first path that extends along a center axis of the treatment unit toward the proximal end side from the first opening, and a second path that extends from a proximal end of the first path to the second opening, and the second path extends along a direction oblique to the longitudinal axis.

5. The ultrasound probe according to claim 4, wherein the first path and the second path form a junction such that the second path extends toward the side surface part.

6. An ultrasound treatment tool comprising: the ultrasound probe according to claim 1; and a cylinder that covers an outer periphery of the probe body of the ultrasound probe.

7. A treatment unit for an ultrasound probe comprising:
a cutter that includes a distal end surface that defines a first opening, the cutter being configured to cut a bone to be treated;
a shaft that includes:
a proximal end, a distal end, and a side surface part that is adjacent to the proximal end and the distal end;
a path that extends longitudinally within the shaft from the first opening to a second opening, the second opening being provided on the side surface part of the shaft, the path being configured to: allow communication between the first opening and the second opening; and discharge debris resulting from cutting the bone;
a first part that defines a first projection geometry of the treatment unit at the proximal end side; and
a second part that is provided proximally of the first part and defining a second projection geometry, an outline of the first projection geometry encompassing an outline the second projection geometry, the second opening being provided in the second part.

8. The ultrasound probe according to claim 7, wherein the first projection geometry on a proximal side of the cutter that, when viewed along a longitudinal axis, has any one of the following shapes: polygon shape and round shape.

9. The ultrasound probe according to claim 8, wherein:
the second projection geometry on a distal end of the shaft that has any one of the following shapes: polygon shape and round shape.

10. The ultrasound probe according to claim 8, wherein:
the second projection geometry on a distal end of the shaft that has any one of the following shapes: polygon shape and round shape.

\* \* \* \* \*